United States Patent
Garcia et al.

(10) Patent No.: US 7,294,646 B2
(45) Date of Patent: Nov. 13, 2007

(54) MAXI-K CHANNEL BLOCKERS, METHODS OF USE AND PROCESS FOR MAKING THE SAME

(75) Inventors: Maria L. Garcia, Edison, NJ (US); Michael A. Goetz, Scotch Plains, NJ (US); Gregory J. Kaczorowski, Edison, NJ (US); Owen B. McManus, Skillman, NJ (US); Richard L. Monaghan, Morristown, NJ (US); William R. Strohl, Bridgewater, NJ (US); Jan S. Tkacz, Piscataway, NJ (US)

(73) Assignee: Merck & Co. Inc., Rahway, NJ (US)

( * ) Notice: Subject to any disclaimer, the term of this patent is extended or adjusted under 35 U.S.C. 154(b) by 314 days.

(21) Appl. No.: 10/511,731

(22) PCT Filed: Jun. 13, 2003

(86) PCT No.: PCT/US03/18842

§ 371 (c)(1),
(2), (4) Date: Oct. 18, 2004

(87) PCT Pub. No.: WO03/105724

PCT Pub. Date: Dec. 24, 2003

(65) Prior Publication Data

US 2005/0239863 A1    Oct. 27, 2005

Related U.S. Application Data

(60) Provisional application No. 60/389,222, filed on Jun. 17, 2002.

(51) Int. Cl.
*A61K 31/40* (2006.01)
*C07D 487/00* (2006.01)

(52) U.S. Cl. ...................... 514/410; 548/417

(58) Field of Classification Search ................ 514/410; 548/417
See application file for complete search history.

(56) References Cited

U.S. PATENT DOCUMENTS

| | | | |
|---|---|---|---|
| 4,386,098 A | 5/1983 | Woltersdorf, Jr. | |
| 4,416,890 A | 11/1983 | Woltersdorf, Jr. | |
| 4,426,388 A | 1/1984 | Woltersdorf, Jr. | |
| 4,599,353 A | 7/1986 | Bito et al. | |
| 4,668,697 A | 5/1987 | Shepard et al. | |
| 4,797,413 A | 1/1989 | Baldwin et al. | |
| 4,824,857 A | 4/1989 | Goh et al. | |
| 4,863,922 A | 9/1989 | Baldwin et al. | |
| 4,883,819 A | 11/1989 | Bito et al. | |
| 5,001,153 A | 3/1991 | Ueno et al. | |
| 5,153,192 A | 10/1992 | Dean et al. | |
| 5,240,923 A | 8/1993 | Dean et al. | |
| 5,378,703 A | 1/1995 | Dean et al. | |
| 5,541,208 A * | 7/1996 | Garcia et al. ............... | 514/379 |
| 5,573,758 A | 11/1996 | Adorante et al. | |
| 5,925,342 A | 7/1999 | Adorante et al. | |
| 6,924,306 B2 * | 8/2005 | Garcia et al. ............... | 514/452 |
| 2005/0239787 A1 * | 10/2005 | Goetz et al. ................ | 514/249 |

FOREIGN PATENT DOCUMENTS

| | | |
|---|---|---|
| WO | WO 89/10757 | 11/1989 |
| WO | WO 93/22318 | 2/1993 |
| WO | WO 94/28900 | 12/1994 |
| WO | WO 96/33719 | 10/1996 |
| WO | WO 01/70686 | 9/2001 |
| WO | WO 01/70745 | 9/2001 |

OTHER PUBLICATIONS

Staub et al., New Paspalinine Derivatives with Antiinsectan Activity From the Sclerotia of Aspergillus Nomius, Tetrahedron Letters, vol. 34, No. 16, pp. 2569-2572, 1993.*
Stephen R. Moore, et al., Invest. Ophthalmol. Vis. Sci., "Development and Aging of Cell topography in the Human Retinal Pigment Epithelium", (1997), vol. 38, No. 10, pp. 2016-2026.
Robert A. Schumer, Arch. Opthalmol, "The Nerve of Glaucoma", (1994), vol. 112, pp. 37-44.
Dandona, et al., Invest. Ophthalmol. Vis. Sci., "Selective Effects of Experimental Glaucoma on Axonal Transport by Retinal anglion Cells to the Dorsal Lateral Geniculate Nucleus", (1991), vol. 32, No. 5, pp. 1593-1599.

* cited by examiner

*Primary Examiner*—Kamal A. Saeed
*Assistant Examiner*—Susannah Chung
(74) *Attorney, Agent, or Firm*—Sylvia A. Ayler; William Krovatin

(57) ABSTRACT

This invention relates to the use of potent potassium channel blockers or a formulation thereof in the treatment of glaucoma and other conditions related to elevated intraocular pressure in the eye of a patient. This invention also relates to the use of such compounds to provide a neuroprotective effect to the eye of a mammalian species, particularly humans.

6 Claims, No Drawings

MAXI-K CHANNEL BLOCKERS, METHODS OF USE AND PROCESS FOR MAKING THE SAME

This application claims the benefit of provisional application U.S. Ser. No. 60/389,222, filed Jun. 17, 2002.

BACKGROUND OF THE INVENTION

Glaucoma is a degenerative disease of the eye wherein the intraocular pressure is too high to permit normal eye function. Damage eventually occurs to the optic nerve head, resulting in irreversible loss of visual function. If untreated, glaucoma may eventually lead to blindness. Elevated intraocular pressure or ocular hypertension, is now believed by the majority of ophthalmologists to represent the earliest phase in the onset of glaucoma.

Many of the drugs formerly used to treat glaucoma proved unsatisfactory. The early methods of treating glaucoma employed pilocarpine and produced undesirable local effects that made this drug, though valuable, unsatisfactory as a first line drug. More recently, clinicians have noted that many β-adrenergic antagonists are effective in reducing intraocular pressure. While many of these agents are effective for this purpose, there exist some patients with whom this treatment is not effective or not sufficiently effective. Many of these agents also have other characteristics, e.g., membrane stabilizing activity, that become more apparent with increased doses and render them unacceptable for chronic ocular use and can also cause cardiovascular effects.

Although pilocarpine and β-adrenergic antagonists reduce intraocular pressure, none of these drugs manifests its action by inhibiting the enzyme carbonic anhydrase, and thus they do not take advantage of reducing the contribution to aqueous humor formation made by the carbonic anhydrase pathway.

Agents referred to as carbonic anhydrase inhibitors decrease the formation of aqueous humor by inhibiting the enzyme carbonic anhydrase. While such carbonic anhydrase inhibitors are now used to treat intraocular pressure by systemic and topical routes, current therapies using these agents, particularly those using systemic routes are still not without undesirable effects. Because carbonic anhydrase inhibitors have a profound effect in altering basic physiological processes, the avoidance of a systemic route of administration serves to diminish, if not entirely eliminate, those side effects caused by inhibition of carbonic anhydrase such as metabolic acidosis, vomiting, numbness, tingling, general malaise and the like. Topically effective carbonic anhydrase inhibitors are disclosed in U.S. Pat. Nos. 4,386,098; 4,416,890; 4,426,388; 4,668,697; 4,863,922; 4,797,413; 5,378,703, 5,240,923 and 5,153,192.

Prostaglandins and prostaglandin derivatives are also known to lower intraocular pressure. U.S. Pat. No. 4,883,819 to Bito describes the use and synthesis of PGAs, PGBs and PGCs in reducing intraocular pressure. U.S. Pat. No. 4,824,857 to Goh et al. describes the use and synthesis of PGD2 and derivatives thereof in lowering intraocular pressure including derivatives wherein C-10 is replaced with nitrogen. U.S. Pat. No. 5,001,153 to Ueno et al. describes the use and synthesis of 13,14-dihydro-15-keto prostaglandins and prostaglandin derivatives to lower intraocular pressure. U.S. Pat. No. 4,599,353 describes the use of eicosanoids and eicosanoid derivatives including prostaglandins and prostaglandin inhibitors in lowering intraocular pressure.

Prostaglandin and prostaglandin derivatives lower intraocular pressure by increasing uveoscleral outflow. This is true for both the F type and A type of Pgs and hence presumably also for the B, C, D, E and J types of prostaglandins and derivatives thereof. A problem with using prostaglandin derivatives to lower intraocular pressure is that these compounds often induce an initial increase in intraocular pressure, can change the color of eye pigmentation and cause proliferation of some tissues surrounding the eye.

As can be seen, there are several current therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Ophthalmol. Vis. Sci 38, 1997; WO 89/10757, WO94/28900, and WO 96/33719).

SUMMARY OF THE INVENTION

This invention relates to novel indole diterpene natural product and synthetic compounds of formula I:

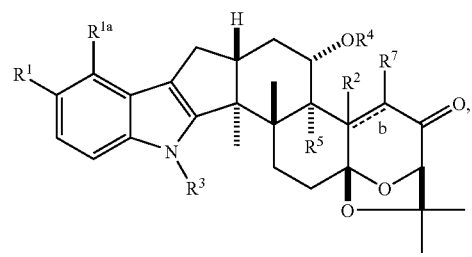

or a pharmaceutically acceptable salt, enantiomer, diastereomer, tautomer or mixture thereof, wherein, $R^1$ and $R^{1a}$ independently are:

(a)

H, (b)

$C_{1-6}$ alkyl (c)

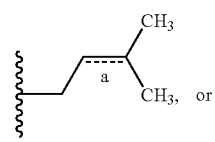

or (d)

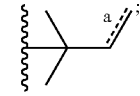

$R^2$ is:

(a) $CO_2C_{1-6}$alkyl, (b) H, (c) OH, or (d) $C_{1-6}$alkyl, when a double bond is not present at b;

$R^3$ is:

(a) H, (b) (C=O)O$C_{1-6}$alkyl or (c) $C_{1-6}$alkyl optionally substituted with OH, $N(R^6)_2$, or $CO_2R^6$;

$R^4$ is (a) H, provided that $R^3$ is not H, (b) $C_{1-6}$alkyl optionally substituted with OH, $N(R^6)_2$, or $CO_2R^6$ or (c)
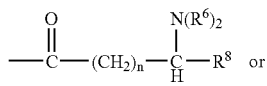

(d)

$R^5$ is:

(a) H, (b) OH, or (c) O$C_{1-6}$alkyl;

$R^6$ is:

(a) H, or (b) $C_{1-6}$alkyl;

$R^7$ is H, or $C_{1-6}$alkyl optionally substituted with OH, $N(R^6)_2$, or $CO_2R^6$;

$R^8$ is H, $C_{1-6}$alkyl, $CH_2$-phenyl, $CH_2$-hydroxyphenyl, $CH_2$-indoyl, $CH_2$-imidazol, $CH_2OR^6$, $CH(OR^6)CH_3$, $(CH_2)_nC(O)NR^6$, $(CH_2)_nCO_2R^6$, $(CH_2)_nSR^6$, or $(CH_2)_n(N^+R^6)_3$;

n is 0-4 and

----- is a double bond optionally and independently present at a or b, and their use as potent potassium channel blockers in the treatment of glaucoma and other conditions which are related to elevated intraocular pressure in the eye of a patient. This invention further relates to compositions containing the novel indole diterpenes of the claimed invention. It also relates to the microorganisms used to make some the compounds of this invention. Also encompassed by this invention is the use of such compounds to provide a neuroprotective effect to the eye of mammalian species, particularly humans. More particularly this invention relates to the treatment of glaucoma and ocular hypertension (elevated intraocular pressure) using the indole diterpene compound having the structural formula I or II:

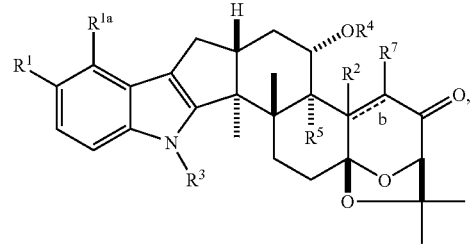

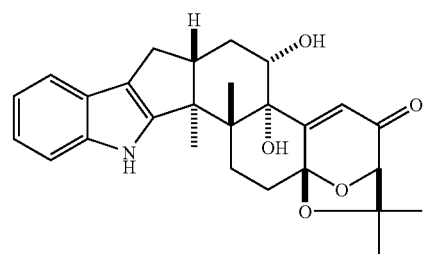

or a pharmaceutically acceptable salt, enantiomer, diastereomer, tautomer or mixture thereof:

wherein, $R^1$ and $R^{1a}$ independently are:

(a) H, (b) $C_{1-6}$ alkyl (c)
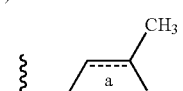

(d)
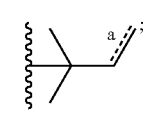

$R^2$ is:

(a) $CO_2C_{1-6}$alkyl, (b) H, (c) OH, or (d) $C_{1-6}$alkyl, when a double bond is not present at b;

$R^3$ is:

(a) H, (b) (C=O)O$C_{1-6}$alkyl or (c) $C_{1-6}$alkyl optionally substituted with OH, $N(R^6)_2$, or $CO_2R^6$;

$R^4$ is (a) H, (b) $C_{1-6}$alkyl optionally substituted with OH, $N(R^6)_2$, or $CO_2R^6$ or (c)

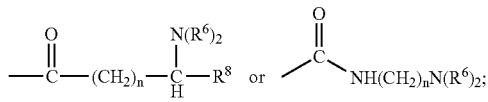

$R^5$ is:
  (a) H,
  (b) OH, or
  (c) $OC_{1-6}$alkyl;

$R^6$ is:
  (a) H, or
  (b) $C_{1-6}$alkyl;

$R^7$ is H, or $C_{1-6}$alkyl optionally substituted with OH, $N(R^6)_2$, or $CO_2R^6$;

$R^8$ is H, $C_{1-6}$alkyl, $CH_2$-phenyl, $CH_2$-hydroxyphenyl, $CH_2$-indoyl, $CH_2OR^6$, $CH(OR^6)CH_3$, $(CH_2)_nC(O)NR^6$, $(CH_2)_nCO_2R^6$, $(CH_2)_nSR^6$, $(CH_2)_n(N^+R^6)_3$, n is 0-4 and

- - - - - is a double bond optionally and independently present at a or b.

This and other aspects of the invention will be realized upon review of the specification as a whole.

DETAILED DESCRIPTION OF THE INVENTION

When any variable (e.g. aryl, heterocycle, $R^{1a}$, $R^6$ etc.) occurs more than one time in any constituent, its definition on each occurrence is independent at every other occurrence. Also, combinations of substituents/or variables are permissible only if such combinations result in stable compounds.

In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

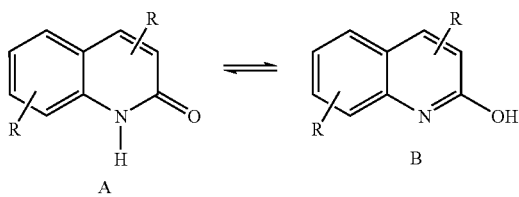

Also included within the scope of this invention are pharmaceutically acceptable salts or esters, where a basic or acidic group is present in a compound of Formula I, such as, for example on the substituted alkyl moiety. When an acidic substituent is present, i.e. —COOH, there can be formed the ammonium, sodium, or calcium salt, and the like, for use as the dosage form. Also, in the case of the —COOH group being present, pharmaceutically acceptable esters may be employed, e.g., acetate, maleate, pivaloyloxymethyl, and the like, and those esters known in the art for modifying solubility or hydrolysis characteristics for use as sustained release or prodrug formulations.

Where a basic group is present, such as amino, acidic salts such as hydrochloride, hydrobromide, acetate, pamoate and the like may be used as the dosage form.

As used herein "alkyl" is intended to include both branched- and straight-chain saturated aliphatic hydrocarbon groups having the specified number of carbon atoms and includes methyl (Me), ethyl (Et), propyl (Pr), butyl (Bu), pentyl, hexyl and the like. "Alkyl" also includes "cycloalkyls" which are saturated carbon ring groups such as cyclopropyl, cyclobutyl, cyclopentyl. "Alkoxy" represents an alkyl group of the indicated number of carbon atoms attached through an oxygen bridge and cyclohexyl (Cyh). "Alkenyl" is intended to include hydrocarbon groups of either a straight or branched configuration with one or more carbon-carbon double bonds which may occur in any stable point along the chain, such as ethenyl, propenyl, butenyl, and the like. "Alkynyl" is intended to include hydrocarbon groups of either a straight or, branched configuration with one or more carbon-carbon triple bonds which may occur in any stable point along the chain, such as ethynyl, propynyl, butynyl, and the like. "Halo" or "halogen" as used herein means fluoro, chloro, bromo and iodo. The term "Boc" refers to t-butyloxy-carbonyl.

An embodiment of this invention is realized when $R^1$, $R^{1a}$ and $R^3$ are hydrogen and all other variables are as originally described.

Still another embodiment of this invention is realized when $R^4$ is

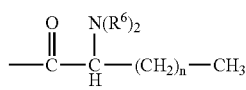

and all other variables are as originally described.

Still another embodiment of this invention is realized when $R^2$ and $R^7$ are hydrogen and $R^4$ is

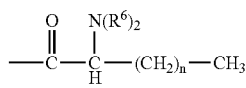

and all other variables are as originally described.

One embodiment of the invention is a composition comprising the indole diterpene of formula I and a pharmaceutically acceptable carrier.

Another embodiment of the invention is the method described above wherein the compound of formula I is applied as a topical formulation.

Yet another embodiment is a method for treating ocular hypertension and/or glaucoma which comprises administering to a patient in need of such treatment a therapeutically effective amount of a compound of formula I or II:

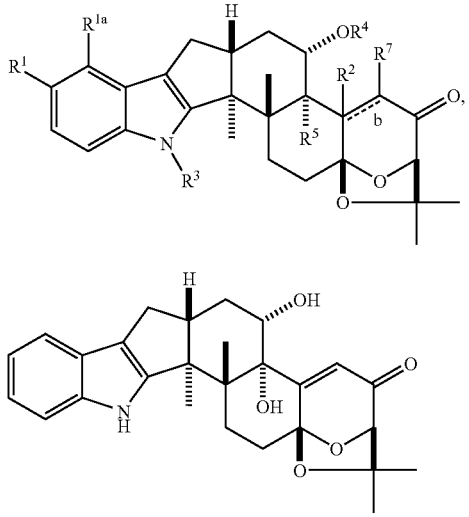

and pharmaceutically acceptable salts, enantiomers, diastereomers, tautomers and mixtures thereof, wherein the variables are as described above.

Yet another embodiment contemplates the method described above wherein the topical formulation is a solution or suspension.

And yet another embodiment is the method described above, which comprises administering a second active ingredient, concurrently or consecutively, wherein the second active ingredient is an ocular hypotensive agent selected from a β-adrenergic blocking agent, adrenergic, agonist, a parasympathomimetic agent, a carbonic anhydrase inhibitor, and a prostaglandin or a prostaglandin derivative.

Another embodiment is the method described above wherein the β-adrenergic blocking agent is timolol, levobunolol, carteolol, optipranolol, metapranolol or betaxolol; the parasympathomimetic agent is pilocarpine, carbachol, or phospholine iodide; adrenergic agonist is iopidine, brimonidine, epinephrine, or dipivephrin, the carbonic anhydrase inhibitor is dorzolamide, acetazolamide, metazolamide or brinzolamide; the prostaglandin is latanoprost or rescula, and the prostaglandin derivative is a hypotensive lipid derived from PGF2α prostaglandins.

A further embodiment is a method for treating macular edema or macular degeneration which comprises administering to a patient in need of such treatment a pharmaceutically effective amount of a compound of structural formula I or II:

-continued or a pharmaceutically acceptable salt, enantiomer, diastereomer, tautomer or mixture thereof, wherein the variables are as described above.

Another embodiment is the method described above wherein the compound of formula I or II is applied as a topical formulation.

Still another embodiment of this invention comprises administering a second active ingredient, concurrently or consecutively, wherein the second active ingredient is an ocular hypotensive agent selected from a β-adrenergic blocking agent, adrenergic agonist, a parasympathomimetic agent, a carbonic anhydrase inhibitor, and a prostaglandin or a prostaglandin derivative.

Another embodiment is the method described above wherein the β-adrenergic blocking agent is timolol, levobunolol, carteolol, optipranolol, metapranolol or betaxolol; the parasympathomimetic agent is pilocarpine, carbachol, or phospholine iodide; adrenergic agonist is iopidine, brimonidine, epinephrine, or dipivephrin, the carbonic anhydrase inhibitor is dorzolamide, acetazolamide, metazolamide or brinzolamide; the prostaglandin is latanoprost or rescula, and the prostaglandin derivative is a hypotensive lipid derived from PGF2α prostaglandins.

A further embodiment is illustrated by a method for increasing retinal and optic nerve head blood velocity or increasing retinal and optic nerve oxygen tension which comprises administering to a patient in need of such treatment a therapeutically effective amount of a compound of Formula I or II:

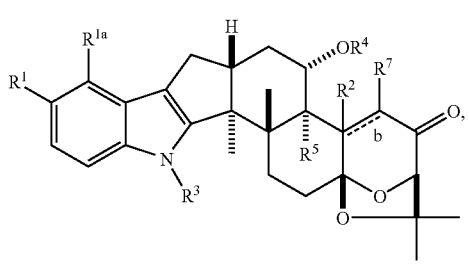

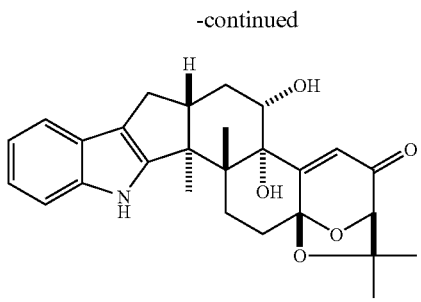

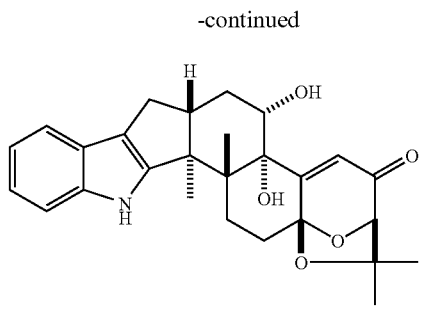

or a pharmaceutically acceptable salt, enantiomer, diastereomer, tautomer or mixture thereof, wherein the variables are as described above.

And another embodiment is the method described above wherein the compound of formula I or II is applied as a topical formulation.

Still another embodiment comprises administering a second active ingredient, concurrently or consecutively, wherein the second active ingredient is an ocular hypotensive agent selected from a β-adrenergic blocking agent, adrenergic agonist, a parasympathomimetic agent, a carbonic anhydrase inhibitor, an EP4 agonist as disclosed in U.S. Ser. No. 60/386,641, filed Jun. 6, 2002, 60/421,402, filed Oct. 25, 2002, 60/457,700, filed Mar. 26, 2003, 60/406,530, filed Aug. 28, 2002 and PCT applications PCT 02/38039, filed Nov. 27, 2002 and PCT 02/38040, filed Nov. 27, 2002, all incorporated by reference in its entirety herein, and a prostaglandin or a prostaglandin derivative.

Another embodiment is the method described above wherein the β-adrenergic blocking agent is timolol, levobunolol, carteolol, optipranolol, metapranolol or betaxolol; the parasympathomimetic agent is pilocarpine, carbachol, or phospholine iodide; adrenergic agonist is iopidine, brimonidine, epinephrine, or dipivephrin, the carbonic anhydrase inhibitor is dorzolamide, acetazolamide, metazolamide or brinzolamide; the prostaglandin is latanoprost or rescula, and the prostaglandin derivative is a hypotensive lipid derived from PGF2α prostaglandins.

Another embodiment of the invention is a method for providing a neuroprotective effect to a mammalian eye which comprises administering to a patient in need of such treatment a therapeutically effective amount of a compound of Formula I or II:

or a pharmaceutically acceptable salt, enantiomer, diastereomer, tautomer or mixture thereof, wherein the variables are as described above.

Also within the scope of the invention is the method described above wherein the compound of Formula I or II is applied as a topical formulation.

Still another embodiment comprises administering a second active ingredient, concurrently or consecutively, wherein the second active ingredient is an ocular hypotensive agent selected from a β-adrenergic blocking agent, adrenergic agonist, a parasympathomimetic agent, a carbonic anhydrase inhibitor, and a prostaglandin or a prostaglandin derivative.

Another embodiment is the method described above wherein the β-adrenergic blocking agent is timolol, levobunolol, carteolol, optipranolol, metapranolol or betaxolol; the parasympathomimetic agent is pilocarpine, carbachol, or phospholine iodide; adrenergic agonist is iopidine, brimonidine, epinephrine, or dipivephrin, the carbonic anhydrase inhibitor is dorzolamide, acetazolamide, metazolamide or brinzolamide; the prostaglandin is latanoprost or rescula, and the prostaglandin derivative is a hypotensive lipid derived from PGF2α prostaglandins.

Also contemplated to be within the scope of the present invention is a topical formulation of Compound I or II as described above wherein the topical formulation also contains xanthan gum or gellan gum.

Examples of compounds of this invention are:

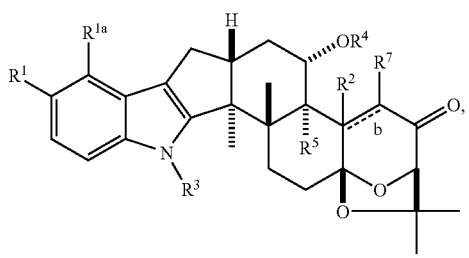

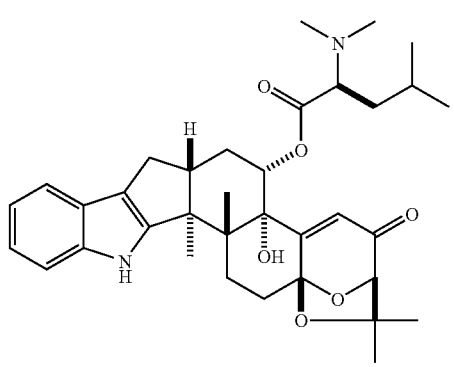

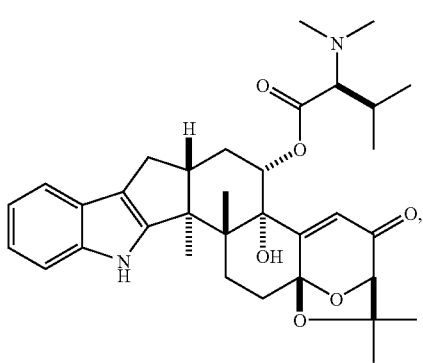

or a pharmaceutically acceptable salt, enantiomer, diastereomer, tautomer or mixture thereof.

This invention is also concerned with a process for making a compound of the formula Ia or Ib:

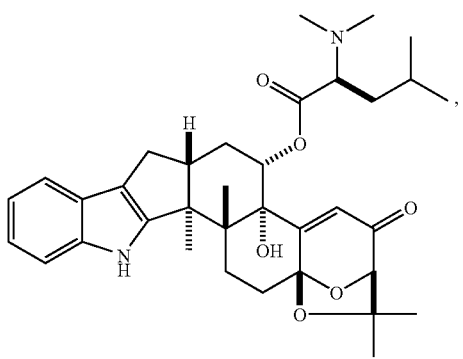

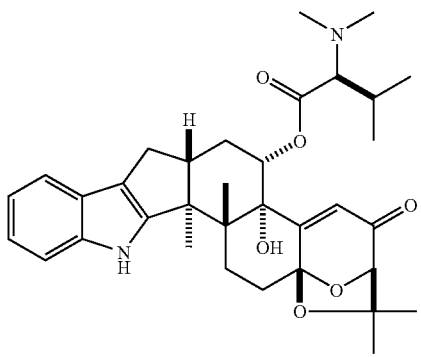

or a pharmaceutically acceptable salt, enantiomer, diastereomer, tautomer or mixture thereof, using microbiological strain *Aspergillus alliaceus* (ATCC Nos. 16891 or PTA-4210), *Aspergillus nomius* (ATCC No. 15546 or PTA-4211), or *Aspergillus nomius* (ATCC No. PTA-4212) for the compound of formula Ia and *Aspergillus nomius* (ATCC No. 15546 or PTA-4211) or *Aspergillus nomius* (ATCC No. PTA-4212) for the compound of formula Ib. Also included in the scope of this invention is microbiological strain *Aspergillus alliaceus* ATCC No. 16891 (PTA-4210).

The invention is described herein in detail using the terms defined below unless otherwise specified.

Also included within the scope of this invention are pharmaceutically acceptable salts or esters, where a basic or acidic group is present in a compound of Formula I.

This invention is also concerned with a method of treating ocular hypertension or glaucoma by administering to a patient in need thereof one of the compounds of formula I or II in combination with an ocular hypotensive agent selected from a β-adrenergic blocking agent such as timolol, optipranolol, levobunolol, metapranolol, carteolol, betaxalol and the like, a parasympathomimetic agent such as pilocarpine, carbachol, phospholine iodide, and the like, adrenergic agonist such as iopidine, brimodine, epinephrine, dipivephrin, and the like, carbonic anhydrase inhibitor such as dorzolamide, acetazolamide, metazolamide or brinzolamide, a prostaglandin such as latanoprost, rescula, S1033 or a prostaglandin derivative such as a hypotensive lipid derived from PGF2α prostaglandins. An example of a hypotensive lipid (the carboxylic acid group on the α-chain link of the basic prostaglandin structure is replaced with electrochemically neutral substituents) is that in which the carboxylic acid group is replaced with a $C_{1-6}$ alkoxy group such as $OCH_3$ ($PGF_{2\alpha}$ 1-$OCH_3$), or a hydroxy group ($PGF_{2\alpha}$ 1-OH).

Preferred potassium channel blockers are calcium activated potassium channel blockers. More preferred potassium channel blockers are high conductance, calcium activated potassium (maxi-K) channel blockers. Maxi-K channels are a family of ion channels that are prevalent in neuronal, smooth muscle and epithelial tissues and which are gated by membrane potential and intracellular $Ca^{2+}$.

Intraocular pressure (IOP) is controlled by aqueous humor dynamics. Aqueous humor is produced at the level of the non-pigmented ciliary epithelium and is cleared primarily via outflow through the trabecular meshwork. Aqueous humor inflow is controlled by ion transport processes. It is thought that maxi-K channels in non-pigmented ciliary epithelial cells indirectly control chloride secretion by two mechanisms; these channels maintain a hyperpolarized membrane potential (interior negative) which provides a driving force for chloride efflux from the cell, and they also provide a counter ion ($K^+$) for chloride ion movement. Water moves passively with KCl allowing production of aqueous humor. Inhibition of maxi-K channels in this tissue would diminish inflow. Maxi-K channels have also been shown to control the contractility of certain smooth muscle tissues, and, in some cases, channel blockers can contract quiescent muscle, or increase the myogenic activity of spontaneously active tissue. Contraction of ciliary muscle would open the trabecular meshwork and stimulate aqueous humor outflow, as occurs with pilocarpine. Therefore maxi-K channels could profoundly influence aqueous humor dynamics in several ways; blocking this channel would decrease IOP by affecting inflow or outflow processes or by a combination of affecting both inflow/outflow processes.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering of IOP promotes increased blood flow to the retina and optic nerve. Accordingly, this invention relates to a method for treating macular edema, macular degeneration or a combination thereof.

Additionally, macular edema is swelling within the retina within the critically important central visual zone at the posterior pole of the eye. An accumulation of fluid within the retina tends to detach the neural elements from one another and from their local blood supply, creating a dormancy of visual function in the area.

Glaucoma is characterized by progressive atrophy of the optic nerve and is frequently associated with elevated intraocular pressure (IOP). It is possible to treat glaucoma, however, without necessarily affecting IOP by using drugs that impart a neuroprotective effect. See Arch. Ophthalmol. Vol. 112, January 1994, pp. 37-44; Investigative Ophthamol. & Visual Science, 32, 5, April 1991, pp. 1593-99. It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof.

The maxi-K channel blockers used are preferably administered in the form of ophthalmic pharmaceutical compositions adapted for topical administration to the eye such as solutions, ointments, creams or as a solid insert. Formulations of this compound may contain from 0.01 to 5% and especially 0.5 to 2% of medicament. Higher dosages as, for example, about 10% or lower dosages can be employed provided the dose is effective in reducing intraocular pressure, treating glaucoma, increasing blood flow velocity or oxygen tension or providing a neuroprotective effect. For a single dose, from between 0.001 to 5.0 mg, preferably 0.005 to 2.0 mg, and especially 0.005 to 1.0 mg of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mammalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The maxi-K channel blocker of formula Ia is made by a microbiological process employing the strain *Aspergillus alliaceus* (MF4946). This strain, ATCC 16891 (PTA-4210), is available from the American Type Culture Collection located at 12301 Parklawn Drive in Rockville, Md.

Maxi-K channel blockers formula Ia and Ib can be produced by a microbiological process employing the strain *Aspergillus nomius* (MF6296), which has been deposited at the American Type Culture Collection as ATCC 15546 (PTA-4211). The compound of formula Ia and Ib can also be produced by a microbiological process employing the strain *Aspergillus nomius* (MF6875), which has been deposited at the American Type Culture Collection as ATCC 15546 (PTA-4212).

Compounds Ia and Ib used in the present invention can be made by a fermentation process for producing potassium channel antagonists comprising:

(a) inoculating seed medium (Table 1) with mycelia and conidia of *Aspergillus alliaceus* MF4946=ATCC 16891 (PTA-4210), *Aspergillus nomius* MF6296=ATCC 15546 (PTA-4211) or *Aspergillus nomius* MF6875=ATCC 15546 (PTA-4212) depending upon which compound is desired.

(b) incubating the inoculated fungal fermentation at room temperature (20-30° C.) under humid conditions with constant fluorescent light, preferably with shaking or without agitation most preferably on a rotary shaker with a 5-cm throw at 220 rpm if fermented in a liquid medium by *A. alliaceus*, at a slower tumbling rpm in a solid medium by *A. alliaceus* or statically if fermented on a solid substrate by either *A. nomius* strain.

(c) using the culture produced in step (b) to inoculate a liquid production medium or a solid substrate medium and further incubating under the conditions defined in step (b) to produce Compound Ia or Ib.

Maximal accumulation of compounds in the fermentation broth occurs between 7-30 days. The invention further comprises a step (d) in which the compounds produced in the fermentation broth under suitable defined and controlled conditions are purified and isolated from the broth. Suitable isolation procedures include, for example, extraction of the culture medium with a solvent, preferably methylethylketone for *A. alliaceus* fermentations and hexane for *A. nomius* fermentations. The strains ATCC-16891 (PTA-4210), ATCC 15546 (PTA-4211), and ATCC 15546 (PTA-4212) are described as follows:

All strains listed below were 3-point inoculated on 100 mm Petri dishes grown at 25 C for 14 days in the dark with no humidity control. CYA is Czapek's yeast autolysate agar and BMEA is Blakeslee's malt extract agar. Recipes for these media are contained in Raper, K. and Fennell, D. 1965. The genus *Aspergillus*. Williams & Wilkins, Co. 686 pp. Color standards in parentheses are from Kornerup, A. and Wanscher, J. 1978. Methuen handbook of colour. London: Eyre Methuen. 252 pp.

*Aspergillus alliaceus* (ATCC16891=PTA-4210=MF4946=E-003478)

Macroscopic

On CYA attaining a diameter of 65-70 mm. Culture mat cottony to woolly with small tufts of thick, white mycelium, white. Conidiogenesis sparse, limited to the outer edge of the culture, light yellow. Moderate black sclerotia. Reverse uncolored, sulcate. Exudate clear, few large droplets. Soluble pigment absent.

On BMEA attaining a diameter of 65-70 mm. Culture mat cottony, sparse, aerial mycelium uncolored near edge to white at colony center. Conidiogenesis limited to colony edge, light yellow. Few large black sclerotia. Reverse, exudate and soluble pigment absent.

Microscopic

Conidial heads small, light yellow, radiate, splitting into large, divergent sections with age (14-21 days). Conidiophores almost 1.0 mm long, more commonly 500-750µ, walls finely echinulate, up to 1µ thick. Vesicles globose, 25-40µ. Sterigmata biseriate, primary series 6-9µ long, secondary series 5-8µ both series 2-3µ wide. Conidia globose, smooth, 2-3µ in diameter. Sclerotia large, ovate to elliptical, 1-3 mm, starting out as white turning black and forms white tips with age.

*Aspergillus nomius* (=ATCC15546=PTA-4211=NRRL 13137=MF6296) and (=ATCC15546-PTA-1412=MF6875)

Macroscopic

On CYA, attaining a diameter of 65-70 mm. Culture mat white, cottony to woolly over which abundant conidiophores are present, filling most of the culture dish, ranging in color from brownish green (4C8, 4C7) at the margin of the plate to a dark olive (4E8, 4E7) towards the center of the colony. Reverse light orange brown (5B6, 5B4), sulcate. Few black sclerotia present. Soluble pigment and exudate absent On BMEA, attaining a diameter of 65-70 mm. Culture mat sparse, cottony, white aerial mycelium. Conidiogenesis sparse, light green (30B8, 30C8). Reverse uncolored. Soluble pigment and exudate absent.

Microscopic

Conidial heads radiate, splitting into poorly defined columns, typically 500-600µ in diameter. Conidiophores roughened, thick walled, hyaline, usually 1-2 mm in length and usually up to 10µ wide. Vesicles elongate when young to subglobose to globose with age, mostly 30-50µ in diameter. Sterigmata usually in biseriate, with phialides 6-10µ long by 4-5µ wide. Conidia coarsely echinulate, globose to subglobose, 3-5µ in diameter. Sclerotia globose to subglobose, dark brown to black, 400-700µ in diameter.

The active compound is extracted from the mycelial growth of the culture with a suitable solvent, such as alcoholic or oxygenated solvent such as an ester or ketone. The preferred solvent for extraction is methylethylketone for liquid fermentations and hexane for solid substrate fermentations. The solution containing the desired compound is concentrated and then subjected to chromatographic separation to isolate Compound I from the cultivation medium.

The preferred sources of carbon in the nutrient medium include glycerol, glucose, sucrose, mannitol, lactose, sorbitol, starch, dextrin, other sugars and sugar alcohols, starches and other carbohydrates, or carbohydrates derivatives, and the like. Other sources which may be included are complex nutrients such as corn meal, oat flour, millet, rice, cracked corn, and the like. The exact quantity of the carbon source which is utilized in the medium will depend, in part, upon the other ingredients in the medium, but it is usually found that an amount of carbohydrate between 0.5 and 40 percent by weight of the medium is satisfactory. These carbon sources can be used individually or several such carbon sources may be combined in the same medium.

The preferred sources of nitrogen are yeast extract, yellow corn meal, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids such as methionine, phenylalanine, serine, alanine, proline, glycine, arginine or threonine, and the like. The various sources of nitrogen can be used alone or in combination in amounts ranging from 0.2 to 10 percent by weight of the medium.

The carbon and nitrogen sources, though advantageously employed in combination, need not be used in their pure form because less pure materials which contain traces of growth factors and considerable quantities of mineral nutrients are also suitable for use. When desired, there may be added to the medium inorganic salts, sodium, potassium, magnesium, calcium, phosphate, sulfate, chloride, carbonate, and like ions which can be incorporated in the culture medium as sodium or calcium carbonate, sodium or potassium phosphate, sodium or potassium chloride, sodium or potassium iodide, magnesium salts, copper salts, cobalt salts, and the like. Also included are trace metals such as cobalt, manganese, iron, molybdenum, zinc, cadmium, copper, and the like. The various sources of inorganic salts can be used alone or in combination in amounts ranging from 0.1 to 1.0, and trace elements ranging from 0.001 to 0.1 percent by weight of the medium.

If necessary, especially when the culture medium foams seriously, a defoaming agent, such as polypropylene glycol 2000 (PPG-2000), liquid paraffin, fatty oil, plant oil, mineral oil or silicone may be added.

Submerged aerobic fermentation conditions in fermentors are preferred for the production of Compound Ia or Ib in large amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of Compound Ia or Ib. Accordingly, it is desirable first to produce a vegetative inoculum of the organism by inoculating a relatively small quantity of culture medium with spores or mycelia of the organism produced in a "slant," or from previously prepared frozen mycelia, and culturing the inoculated medium, also called the "seed medium", and then aseptically transferring the cultured vegetative inoculum to large tanks. The seed medium, in which the inoculum is produced may be seen in Table 1 and is generally autoclaved to sterilize the medium prior to inoculation. The seed medium is generally adjusted to a pH between 5 and 8, preferably about 6.8, prior to the autoclaving step by suitable addition of an acid or base, preferably in the form of a dilute solution of hydrochloric acid or sodium hydroxide. Growth of the culture in this seed medium is maintained between 22° C. and 37° C., preferably 25° C. Incubation of culture ATCC No. 16891 or ATCC No. 15546 in a seed medium, preferably that in Table 1, is usually conducted for a period of about 2 to 6 days, preferably 3 to 4 days, with shaking, preferably on a rotary shaker operating at 220 rpm with a 5 cm throw; the length of incubation time may be varied according to fermentation conditions and scales. If appropriate, a second stage seed fermentation may be carried out in the seed medium (Table 1) for greater production of mycelial mass by inoculating fresh seed medium with a portion of the culture growth and then incubating under similar conditions but for a shortened period. The resulting growth then may be employed to inoculate, a production medium, preferably the Liquid Production Medium (Table 2). The fermentation liquid production medium inoculated with the seed culture growth is incubated for 3 to 28 days, usually 7 to 11 days, with agitation. Agitation and aeration of the culture mixture may be accomplished in a variety of ways. Agitation may be provided by a propeller or similar mechanical agitation equipment, by revolving or shaking the fermentation mixture within the fermentor, by various pumping equipment or by the passage of sterile air through the medium. Aeration may be effected by passing sterile air through the fermentation mixture.

Preferred seed and production media for carrying out the fermentation include the following media:

TABLE 1

Composition of Seed Medium

| SEED MEDIUM | | TRACE ELEMENTS SOLUTION #2 | |
|---|---|---|---|
| Component | (g/L) | Component | (g/L) |
| Corn steep powder | 2.5 | FeSO$_4$.7H$_2$O | 1.0 |
| Tomato paste | 40.0 | MnSO$_4$.H$_2$O | 1.0 |
| Oat flour | 10.0 | CuCl$_2$.2H$_2$O | 0.025 |
| Glucose | 10.0 | CaCl$_2$.H$_2$O | 0.1 |
| Trace elements solution #2 | 10.0 ml/L | H$_3$BO$_3$ | 0.056 |
| | | (NH$_4$)$_6$Mo$_7$O$_{24}$.4H$_2$O | 0.019 |
| | | ZnSO$_4$.7H$_2$O | 0.2 | pH to 6.8
Trace elements prepared in 0.6N HCl

The seed medium was prepared with distilled water and dispensed at 50 ml/250 ml non-baffled Erlenmeyer flask with cotton closures. Sterilization was at 121° C. for 20 minutes.

TABLE 2

Composition of Production Media

A. Solid substrate production medium

1. Solid portion:

675 cc large particle vermiculite were added to a 2-liter roller bottle. This was plugged with a latex closure and autoclaved for 60 min., plus 30 min. dry.

2. Liquid portion:

| Component | (g/L) |
|---|---|
| Dextrose | 150.0 |
| Urea | 4.0 |
| NZ amine Type A | 4.0 |
| K$_2$HPO$_4$ | 0.5 |
| MgSO$_4$.7H$_2$O | 0.25 |
| KCl | 0.25 |
| ZnSO$_4$.7H$_2$O | 0.9 |
| CaCO$_3$ | 16.5 |

No pH adjustment
The production medium was prepared with distilled water, dispensed at 220 ml/500 ml bottle and sterilized at 121° C. for 15 minutes.
Wherein NZ Amine Type A is a protein hydrolysate (an enzymatic digest of casein), manufacturer is Quest International (Norwich, NY).

B. Liquid production medium

| Component | g/L | Trace elements Component | g/L |
|---|---|---|---|
| Glycerol | 100.0 | ZnSO$_4$.7H$_2$O | 0.5 |
| Glucose | 70.0 | CuSO$_4$.5H$_2$O | 0.05 |
| L-tryptophan | 0.7 | FeSO$_4$.7H$_2$O | 0.5 |
| NH$_4$Cl | 3.0 | MnSO$_4$.5H$_2$O | 0.1 |
| Monosodium glutamate | 10.0 | CoCl$_2$.6H$_2$O | 0.04 |
| Amicase | 8.0 | | |
| MES buffer | 20.0 | | |
| K$_2$HPO$_4$ | 1.0 | | |
| MgSO$_4$.7H$_2$O | 0.5 | | |
| 85% lactic acid | 5.0 ml | | |
| Trace elements | 20.0 ml | | |
| CaCO$_3$ | 1.0 | | |

Prepared in 0.6N HCl
pH to 6.0 before adding CaCO$_3$
The liquid production medium was prepared with distilled water and dispensed at 50 ml/250 ml non-baffled Erlenmeyer flask with cotton closures. Sterilization was at 121° C. for 15 minutes.

Fermentor Process
Seed Medium (the same as listed in Table 1):

| Component | (g/L) |
|---|---|
| Corn Steep Liquor | 2.5 |
| Tomato Paste | 40 |
| Oat Flour | 10 |
| Glucose | 10 |
| Trace Elements #2 | 10 (ml) |

Production Medium:

| Component | (g/L) |
|---|---|
| Glycerol | 100.0 |
| Glucose | 70.0 |
| L-tryptophan | 0.7 |
| NH$_4$Cl | 3.0 |
| MSG | 10.0 |
| Amicase | 8.0 |
| MES | 20.0 |
| K$_2$HPO$_4$ | 1.0 |

TABLE 2-continued

Composition of Production Media

| | |
|---|---|
| MgSO$_4$.7H$_2$O | 0.5 |
| 85% Lactic Acid | 5.0 (ml) |
| Trace Elements 1B | 20.0 (ml) |
| Adjust pH to 6.0, then add: | |
| CaCO$_3$ | 1.0 |
| P2000 | 1 ml/L |

Trace Elements 1B:

| Component | (g/L) |
|---|---|
| Prepared in 0.6N HCl: | |
| ZnSO$_4$.7H$_2$O | 0.5 |
| CuSO$_4$.5H$_2$O | 0.05 |
| FeSO$_4$.7H$_2$O | 0.5 |
| MnSO$_4$.H$_2$O | 0.1 |
| CoCl$_2$.6H$_2$O | 0.04 |

Procedure:

A two-stage seed process is used in scale-up: the first stage is a 250 mL flask of seed medium, grown at 22-25° C. and 220 rpm for 48 hours. The second stage is a 2 L flask of seed medium inoculated with 0.5-1 mL of the first stage seed and grown at the same conditions for 48-72 hours. The fermentors are set with 20-50 L working volume of production medium and sterilized for 25 minutes at 123° C. The fermentors are then inoculated with the second stage seed (2.5-3% inoculum) and set at the following conditions:

| | |
|---|---|
| Temperature | 22-26° C. |
| Pressure | 5.0 psig |
| Airflow | 5.0-15.0 lpm |
| Agitation | 300-700 rpm |
| pH | no control |

The agitation is provided by Rushton impellors and is used to control the Dissolved Oxygen level at or above 30%. Sterile samples are taken and assayed by HPLC starting on the 7$^{th}$ day after inoculation and every 2-3 days after that until production titers level off. The optimum fermentation cycle is 14-17 days.

The following examples are provided to illustrate the present invention and should not be construed as limiting the scope of the invention.

EXAMPLE 1

Production of Compound Ia by Fermentation

Seed: Culture ATCC 16891 was maintained as a lyophilized preparation at 4° C. The contents of one lyo tube were suspended in 50 ml seed medium. (See Table 1 for composition of the seed medium.) The cultures were grown on a gyratory shaker (220 rpm) for 3-4 days at 25° C., 85% relative humidity, until a sufficient amount of biomass was obtained.

Production: The composition of the solid substrate fermentation medium is shown in Table 2. A 1 ml aliquot of each grown seed was placed into 50 ml of the liquid portion of the production medium in 250 ml Erlenmeyer flasks. The flasks were incubated 14-21 days for metabolite production. This was swirled vigorously to disperse the biomass. The contents were dispensed by pouring into a 2-liter roller culture vessel that contained 675 cubic centimeters of steam-sterilized large-particle vermiculite. The contents of the roller bottle were shaken/mixed to insure homogeneous inoculation and coverage. The roller bottles were then incubated horizontally, revolving at approximately 4 rpm on a Wheaton roller apparatus, at 22° C., for 19 days, to obtain secondary metabolite production in the fermentation medium.

The composition of the liquid fermentation medium is shown above in Table 2. A 1 ml aliquot of the grown seed was placed into 50 ml liquid production medium in 250 ml Erlenmeyer flasks. The flasks were incubated 14-21 days, 22° C., 220 rpm, for metabolite production.

EXAMPLE 2

Purification and Identification of Compound Ia or Ib.

The instant compound can be purified from crude extracts of fermentations by a combination of chromatographic methods.

Fermentation broth prepared as described in Example 1, volume 2.0 liters, was exhaustively extracted with vigorous shaking with methyl ethyl ketone. After filtering and evaporating the solvent under reduced pressure, the aqueous suspension was re-extracted with methyl ethyl ketone. After drying, the residue was re-dissolved in 60 ml methylene chloride.

A first fractionation was effected by column chromatography on 80 cc silica gel, eluting with a gradient of ethyl acetate in methylene chloride. The 50:50 (v/v) eluate contained the compound of interest, well removed from major impurities and other indole diterpenes.

The rich cuts were evaporated down. A second step of purification was carried out by gel filtration on Sephadex LH-20 in methanol, affording the compound at 0.75-0.9 column volumes of elution.

The resulting preparation was suitable for HPLC, which was carried out on a Zorbax RxC8 column [2.5×25 cm column, eluted at 8 ml/min with acetonitrile-water 50:50 (v/v) followed by a 100-minute gradient to 100% acetonitrile]. This afforded pure Compound Ia after evaporation of the solvent and freeze-drying.

Chromatographic characteristic: k'=7.0 on a 0.46×25 cm Zorbax RxC8 column maintained at 40° C. and eluted at 1 ml/min with a gradient of 30% to 100% acetonitrile in 0.1% trifluoroacetic acid over 30 minutes.

In similar fashion, Compound Ia was purified from fermentations described in Example 2.

Hexane extracts, amounting to 6.5 liters, were evaporated down. Dissolving in methylene chloride and running a column chromatography step as described above allowed for partial purification of Compound I by removal of massive amounts of other indole diterpenes and other impurities. Further purification was achieved by gel filtration, again, as described above, and a final HPLC step on Zorbax RxC8. to yield both Compound Ia and Ib.

The purified compound was identified by NMR and mass spectrometry.

Compound Ia: MW 590, $C_{35}H_{46}N_2O_6$; M+H obs. at 591.3450, calc. 591.3434.

$^1$H NMR δ 0.92 (3H, d), 0.93 (3H, d), 1.16 (3H, s), 1.29 (3H, s), 1.42 (3H, s), 1.43 (3H, s), 1.53 (2H, m), 1.65 (1H, m), 1.83 (1H, m), 2.01 (1H, dd), 2.08 (1H, m), 2.26 (1H, ddd), 2.37 (6H, s), 2.47 (1H, dd), 2.73 (1H, m), 2.78 (1H, m), 2.87 (1H, m), 2.95 (1H, m), 3.27 (1H, br t), 4.31 (1H, d), 5.39 (1H, dd), 5.50 (1H, br d), 7.04 (1H, m), 7.07 (1H, m), 7.32 (1H, m), 7.42, (1H, m), 7.87 (1H, br s).

$^{13}$C NMR: 16.4, 22.4, 22.8, 23.2, 23.4, 25.3, 27.4, 28.0, 28.7, 28.8, 29.0, 38.4, 41.3, 41.3, 45.5, 51.6, 65.8, 74.8, 78.6, 79.5, 88.7, 104.9, 112.0, 117.7, 118.8, 119.6, 120.0, 121.0, 125.4, 140.4, 151.2, 166.4, 171.1, 196.4.

$^1$H NMR spectra were recorded at 500 MHz in $CD_2Cl_2$ on a Varian Unity 500 NMR spectrometer at 25° C. Chemical shifts are indicated in ppm relative to TMS at zero ppm using the solvent peak as internal standard. Only diagnostic peaks are noted.

Abbreviations: s=singlet, d=doublet, q=quartet, br=broad, m=multiplet, t=triplet.

$^{13}$C NMR spectra were recorded at 125 MHz in $CD_2Cl_2$ on a Varian Unity 500 NMR spectrometer at 25° C.

EXAMPLES 3A-F

Example 3A

Example E-050261-007M+E-050261-008P (Production of 1b by strain ATCC PTA-4212)

Seed: Culture ATCC PTA-4212 was maintained as a lyophilized preparation at 4° C. The contents of one lyo tube were suspended in 50 ml seed medium NAS. (See Table X for composition of the seed medium.) The cultures were grown on gyratory shaker (220 rpm) for 3 days at 25° C., 85% relative humidity, until a sufficient amount of biomass was obtained. A second generation seed was prepared by inoculating a fresh flask of NAS with an aliquot (2ml) of the 3 day growth. The second generation seed was incubated for 1 day at 25 C on a gyratory shaker (220 rpm).

Production: The composition of the solid substrate fermentation media F1+ and RM+ are shown in Table X. An aliquot (2.0 ml) of each grown seed was placed into a 250 ml Erlenmeyer flask containing medium F1+ or RM+. Inoculated flasks were incubated at 25° C., for 22 days. At harvest, completed fermentations were extracted with 75 ml of hexane per flask.

Example 3B

Example E-050263-001S (Production of Ib by strain ATCC PTA-4211)

Seed: Culture ATCC PTA-4211 was maintained as a lyophilized preparation at 4° C. The contents of one lyo tube were suspended in 50 ml seed medium NAS. (See Table X for composition of the seed medium.) The cultures were grown on a gyratory shaker (220 rpm) for 3 days at 25° C., 85% relative humidity, until a sufficient amount of biomass was obtained. A second generation seed was prepared by inoculating a fresh flask of NAS with an aliquot (2 ml) of the 3 day growth. The second generation seed was incubated for 1 day at 25 C on a gyratory shaker (220 rpm).

Production: The composition of the solid substrate fermentation medium 3Q18 is shown in Table X. An aliquot (2.0 ml) of each grown seed was placed into a 250 ml Erlenmeyer flask containing medium 3Q18 Inoculated flasks were incubated at 25° C., for 22 days. At harvest completed fermentations were extracted with 125 ml of hexane per flask.

Example 3C

Example E-050263-001S (Production of Ib by strain ATCC PTA-4211)

Seed: Culture ATCC PTA-4211 was maintained as a frozen vial preparation at −80° C. The contents of one vial were suspended in 50 ml seed medium NASMOD. (See Table X for composition of the seed medium.) The cultures were grown on a gyratory shaker (220 rpm) for 5 days at 25° C., 85% relative humidity, until a sufficient amount of biomass was obtained. A second generation seed was prepared by inoculating a fresh flask of NASMOD with an aliquot (2 ml) of the 5 day growth. The second generation seed was incubated for 2 day at 25 C on a rotary shaker (220 rpm).

Production: The composition of the solid substrate fermentation medium 3Q18 is shown in Table X. An aliquot (2.0 ml) of each grown seed was placed into a 250 ml Erlenmeyer flask containing medium 3Q18 Inoculated flasks were incubated at 25° C., for 14 days. At harvest completed fermentations were extracted with 150 ml of hexane per flask.

Example 3D

Example E-050263-001S (Production of Ib by strain ATCC PTA-4211)

Seed: Culture ATCC PTA-4211 was maintained as a lyophilized preparation at 4° C. The contents of one lyo tube were suspended in 50 ml seed medium NAS. (See Table X for composition of the seed medium.) The cultures were grown on a gyratory shaker (220 rpm) for 3 days at 25° C., 85% relative humidity, until a sufficient amount of biomass was obtained. A second generation seed was prepared by inoculating a fresh flask of NAS with an aliquot (2 ml) of the 3 day growth. The second generation seed was incubated for 1 day at 25 C on a gyratory shaker (220 rpm).

Production: The composition of the solid substrate fermentation medium F1+ is shown in Table X. An aliquot (2.0 ml) of each grown seed was placed into a 250 ml Erlenmeyer flask containing medium F1+ Inoculated flasks were incubated at 25° C., for 22 days. At harvest completed fermentations were extracted with 75 ml of hexane per flask.

Example 3E

Example (Compound Ia) E-050263-014C-(Production of Ia by strain ATCC PTA-4211)

Seed: Culture ATCC PTA-4211 was maintained as a frozen vial preparation at −80° C. The contents of one vial were suspended in one flask of medium 3Q18. (See Table X for composition) The flask was incubated for 13 days at 25° C., 85% relative humidity, until sufficient spores were obtained. Spores were harvested by adding 40 ml of fresh NAS medium to the flask and agitating to disperse the spores throughout the liquid.

Production: The composition of the solid substrate fermentation medium 3Q18 is shown in Table X. An aliquot (1.0 ml) of harvested spores was placed into a 250 ml Erlenmeyer flask containing medium 3Q18 Inoculated flasks were incubated at 30° C., for 9 days. At harvest, completed fermentations were extracted with 125 ml of hexane per flask.

Example 3F

Seed: Culture ATCC PTA-4211 was maintained as a frozen vial preparation at −80° C. The contents of one vial were suspended in 50 ml seed medium KFA. (See Table X for composition of the seed medium.) The cultures were grown without agitation for 19 days at 25° C., 85% relative humidity, until a sufficient amount of biomass was obtained. This growth was diluted with 100 ml of sterile distilled water and agitated vigorously before being used to inoculate production flasks.

Production: The composition of the solid substrate fermentation medium RiceMan is shown in Table X. An aliquot (2.0 ml) of each grown diluted KFA seed was placed into a 250 ml Erlenmeyer flask containing medium RiceMan Inoculated flasks were incubated at 30° C., for 23 days. At harvest completed fermentations were extracted with 125 ml of hexane per flask.

Media Formulations

KF/NAS—Dried Corn Steep 2.5 grams, Tomato paste 40.0 grams, Oat flour 10.0 grams, Glucose 10.0 grams, Trace elements mix #2 10.0 ml., deionized water 1000 ml. pH adjusted to 6.8 with 6N NaOH.

Trace elements mix #2 contains: $FeSO_4.7H_2O$ 1.0 gram, $MnSO_4.H_2O$ 1.0 gram, $CuCL_2.2H_2O$ 0.025 gram, $CaCL_2$ 0.1 gram, $H_3BO_3$ 0.056 gram, $(NH_4)_6Mo_7O_{24}.4H_2O$ 0.019 gram, $ZnSO_4.7H_2O$ 0.2 gram, in 1000 ml 0.6N HCl KFA—KF medium plus agar at 4.0 grams per liter NASMOD—Glucose 10.0 grams, Oat flour 10.0 grams, Dried tomato paste 18.0 grams, Corn Steep powder 2.5 grams, Trace elements mix #2 10.0 ml deionized water 1000 ml pH 6.8 with NaOH. Trace elements mix #2 contains: $FeSO_4.7H_2O$ 1.0 gram, $MnSO_4.H_2O$ 1.0 gram, $CuCL_2.2H_2O$ 0.025 gram, $CaCL_2$ 0.1 gram, $H_3BO_3$ 0.056 gram, $(NH_4)_6Mo_7O_{24}.4H_2O$ 0.019 gram, $ZnSO_4.7H_2O$ 0.2 gram, in 1000 ml 0.6N HCl F1+—Cracked Corn 10.0 grams per 250 ml Erlenmeyer flask, Base Liquid C 10.0 ml. per 250 ml. Erlenmeyer flask, Deionized water 10.0 ml. per 250 ml Erlenmeyer flask. Base liquid C contains: Yeast extract 0.2 gram, $KH_2PO_4$ 0.1 gram, $MgSO_4.7H_2O$ 0.1 gram, Na tartrate 0.1 gram, $FeSO_4.7H_2O$ 0.01 gram, $ZnSO_4.7H_2O$ 0.01 gram, deionized water 1000 ml.

RM+—Brown Rice 10.0 grams per 250 ml Erlenmeyer flask, Base Liquid B 20 ml per 250 ml Erlenmeyer flask. Base Liquid B contains: Yeast extract 1.0 gram, Na tartrate 0.5 gram, $KH_2PO_4$ 0.5 gram, $MgSO_4.7H_2O$ 0.5 gram, Trace elements mix 1B 10 ml.

Trace Elements Mix 1B contains: $ZnSO_4.7H_2O$ 0.5 gram, $CuSO_4.5H_2O$ 0.05 gram, $FeSO_4.7H_2O$ 0.5 gram, $MnSO_4.H_2O$ 0.1 gram, $CoCL_2.6H_2O$ 0.04 gram in 1000 ml of 0.6N HCL.

3Q18—Brown Rice 24.5 grams per 250 ml Erlenmeyer flask, Base Liquid A 50 ml per 250 ml Erlenmeyer flask. Base Liquid A contains: Mannitol 125 grams, Glucose 12.5 grams, L-Tryptophan 10.0 grams, Yeast extract 5.0 grams, $KH_2PO_4$ 5.0 grams, deionized water 1000 ml.

RiceMan—Brown Rice 22.0 grams, Base Liquid 18 L 35 ml per 250 ml Erlenmeyer flask. Base Liquid 18 L contains: Mannitol 125 grams, Glucose 12.5 grams, L-Tryptophan 4.0 grams, Yeast extract 5.0 grams, $KH_2PO_4$ 5.0 grams, deionized water 1000 ml.

EXAMPLE 4

Electrophysiological Assays of Compound Effects on High-conductance Calcium-activated Potassium Channels Methods:

Patch clamp recordings of currents flowing through high-conductance calcium-activated potassium (Maxi-K) channels were made from membrane patches excised from CHO cells constitutively expressing the α-subunit of the Maxi-K channel or HEK293 cells constitutively expressing both α- and β1-subunits using conventional techniques (Hamill et al., 1981, Pflügers Archiv. 391, 85-100) at room temperature. Glass capillary tubing (Garner #7052) was pulled in two stages to yield micropipettes with tip diameters of approximately 1-2 microns. Pipettes were typically filled with solutions containing (mM): 150 KCl, 10 Hepes (4-(2-hydroxyethyl)-1-piperazine methanesulfonic acid), 1 Mg, 0.01 Ca, and adjusted to pH 7.20 with 3.7 mM KOH. After forming a high resistance (>$10^9$ ohms) seal between the plasma membrane and the pipette, the pipette was withdrawn from the cell, forming an excised inside-out membrane patch. The patch was excised into a bath solution containing (mM): 150 KCl, 10 Hepes, 5 EGTA (ethylene glycol bis(β-aminoethyl ether)-N,N,N',N'-tetraacetic acid), sufficient Ca to yield a free Ca concentration of 1-5 μM, and the pH was adjusted to 7.2 with KOH. For example, 4.193 mM Ca was added to give a free concentration of 1 μM at 22° C. An EPC9 amplifier (HEKA Elektronic, Lambrect, Germany) was used to control the voltage and to measure the currents flowing across the membrane patch. The input to the headstage was connected to the pipette solution with a Ag/AgCl wire, and the amplifier ground was connected to the bath solution with a Ag/AgCl wire covered with a tube filled with agar dissolved in 0.2 M KCl. The identity of Maxi-K currents was confirmed by the sensitivity of channel open probability to membrane potential and intracellular calcium concentration.

Data acquisition was controlled by PULSE software (HEKA Elektronic) and stored on the hard drive of a MacIntosh computer (Apple Computers) for later analysis using PULSEFIT (HEKA Elektronic) and Igor (Wavemetrics, Oswego, Oreg.) software.

Results:

The effects of the compounds of the present invention on Maxi-K channels were examined in excised inside-out membrane patches. The membrane potential was held at −80 mV and brief voltage steps to positive membrane potentials (typically +50 mV) were applied once per 15 seconds to transiently open Maxi-K channels. The fraction of channels blocked in each experiment was calculated from the reduction in peak current caused by application of the specified compound to the internal side of the membrane patch. As a positive control in each experiment, Maxi-K currents were eliminated at pulse potentials after the patch was transiently exposed to a low concentration of calcium (<10 nM) made by adding 1 mM EGTA to the standard bath solution with no added calcium. A 1 nM concentration of compound Ia caused an 88% decrease in Maxi-K channel currents. After removal of compound from the bath, little or no recovery of peak current amplitude was observed within 15 minutes.

EXAMPLE 5

The activity of the compound can also be quantified by the following assay.

The identification of inhibitors of the Maxi-K channel is based on the ability of expressed Maxi-K channels to set cellular resting potential after transfection of both alpha and beta1 subunits of the channel in HEK-293 cells and after being incubated with potassium channel blockers that selectively eliminate the endogenous potassium conductances of HEK-293 cells. In the absence of Maxi-K channel inhibitors, the transfected HEK-293 cells display a hyperpolarized membrane potential, negative inside, close to $E_K$ (–80 mV) which is a consequence of the activity of Maxi-K channels. Blockade of the Maxi-K channel by incubation with Maxi-K channel blockers will cause cell depolarization. Changes in membrane potential can be determined with voltage-sensitive fluorescence resonance energy transfer (FRET) dye pairs that use two components, a donor coumarin ($CC_2DMPE$) and an acceptor oxanol ($DiSBAC_2(3)$).

Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, a decrease in FRET. Thus, the ratio change (donor/acceptor) increases after membrane depolarization, which determines if a test compound actively blocks the maxi-K channel.

The HEK-293 cells were obtained from American Type Culture Collection, 12301 Parklawn Drive, Rockville, Md., 20852 under accession number ATCC CRL-1573. Any restrictions relating to public access to the cell line shall be irrevocably removed upon patent issuance.

Transfection of the alpha and beta1 subunits of the maxi-K channel in HEK-293 cells was carried out as follows: HEK-293 cells were plated in 100 mm tissue culture treated dishes at a density of $3 \times 10^6$ cells per dish, and a total of five dishes were prepared. Cells were grown in a medium consisting of Dulbecco's Modified Eagle Medium (DMEM) supplemented with 10% Fetal Bovine serum, 1× L-Glutamine, and 1× Penicillin/Streptomycin, at 37° C., 10% $CO_2$. For transfection with Maxi-K hα(pCIneo) and Maxi-K hβ1(pIRESpuro) DNAs, 150 μl FuGENE6™ was added drop-wise into 10 ml of serum free/phenol-red free DMEM and allowed to incubate at room temperature for 5 minutes. Then, the FuGENE6™ solution was added drop-wise to a DNA solution containing 25 μg of each plasmid DNA, and incubated at room temperature for 30 minutes. After the incubation period, 2 ml of the FuGENE6™/DNA solution was added drop-wise to each plate of cells and the cells were allowed to grow two days under the same conditions as described above. At the end of the second day, cells were put under selection media that consisted of DMEM supplemented with both 600 μg/ml G418 and 0.75 μg/ml puromycin. Cells were grown until separate colonies were formed. Five colonies were collected and transferred to a 6 well tissue culture treated dish. A total of 75 colonies were collected. Cells were allowed to grow until a confluent monolayer was obtained. Cells were then tested for the presence of Maxi-K channel alpha and beta1 subunits using an assay that monitors binding of $^{125}$I-iberiotoxin-D19Y/Y36F to the channel. Cells expressing $^{125}$I-iberiotoxin-D19Y/Y36F binding activity were then evaluated in a functional assay that monitors the capability of Maxi-K channels to control the membrane potential of transfected HEK-293 cells using fluorescence resonance energy transfer (FRET) Aurora Biosciences technology with a VIPR instrument. The colony giving the largest signal to noise ratio was subjected to limiting dilution. For this, cells were resuspended at approximately 5 cells/ml, and 200 μl were plated in individual wells in a 96 well tissue culture treated plate, to add ca. one cell per well. A total of two 96 well plates were made. When a confluent monolayer was formed, the cells were transferred to 6 well tissue culture treated plates. A total of 62 wells were transferred. When a confluent monolayer was obtained, cells were tested using the FRET-functional assay. Transfected cells giving the best signal to noise ratio were identified and used in subsequent functional assays.

For Functional Assays:

The transfected cells (2E+06 Cells/mL) are then plated on 96-well poly-D-lysine plates at a density of about 100,000 cells/well and incubated for about 16 to about 24 hours. The medium is aspirated of the cells and the cells washed one time with 100 μl of Dulbecco's phosphate buffered saline (D-PBS). One hundred microliters of about 9 μM coumarin ($CC_2DMPE$)-0.02% pluronic-127 in D-PBS per well is added and the wells are incubated in the dark for about 30 minutes. The cells are washed two times with 100 μl of Dulbecco's phosphate-buffered saline and 100 μl of about 4.5 μM of oxanol ($DiSBAC_2(3)$) in (mM) 140 NaCl, 0.1 KCl, 2 $CaCl_2$, 1 $MgCl_2$, 20 Hepes-NaOH, pH 7.4, 10 glucose is added. Three micromolar of an inhibitor of endogenous potassium conductance of HEK-293 cells is added. A maxi-K channel blocker is added (about 0.01 micromolar to about 10 micromolar) and the cells are incubated at room temperature in the dark for about 30 minutes.

The plates are loaded into a voltage/ion probe reader (VIPR) instrument, and the fluorescence emission of both $CC_2DMPE$ and $DiSBAC_2(3)$ are recorded for 10 sec. At this point, 100 μl of high-potassium solution (mM): 140 KCl, 2 $CaCl_2$, 1 $MgCl_2$, 20 Hepes-KOH, pH 7.4, 10 glucose are added and the fluorescence emission of both dyes recorded for an additional 10 sec. The ratio $CC_2DMPE/DiSBAC_2(3)$, before addition of high-potassium solution equals 1. In the absence of maxi-K channel inhibitor, the ratio after addition of high-potassium solution varies between 1.65-2.0. When the maxi-K channel has been completely inhibited by either a known standard or test compound, this ratio remains at 1. It is possible, therefore, to titrate the activity of a maxi-K channel inhibitor by monitoring the concentration-dependent change in the fluorescence ratio. The activity for blocking maxi-K channels by compounds Ia and Ib is 100 nM or less.

EXAMPLE 6

Intraocular Pressure (IOP) Measurements in Rabbits

Normotensive Dutch Belted rabbits (2.3 kg) of either sex were maintained on a 12-hour light/dark cycle during these experiments. Intraocular pressure (IOP) was measured using a calibrated pneumatonometer (Alcon Applanation Pneumatonograph), and results expressed in millimeters of mercury (mmHg). Before tonometry, one drop of 0.05% proparacaine was applied to the corneas to minimize any discomfort to the animal. Two base-line (control) readings were taken at (–0.5 and 0 hr.) after which Compounds I, Ia or II were administered topically (unilaterally applied into the conjunctival sac) in a 25 μl volume with the contralateral (fellow) eye receiving an equal volume of vehicle. A masked design was utilized, where the person involved in drug administration and measurement of IOP had no knowledge of the solutions' contents. Subsequently, IOP measurements were taken at 0.5, 1, 2, 3, 4, 5 and 6 hr after topical applications of drug. At the end of each day's measurements, stability of the tonometer was determined using the calibrator/verifier.

Results

Unilateral topical application of Compounds Ia, or Ib (0.5, 0.1 and 0.01%) to normal Dutch Belted rabbits elicited reduction of IOP of 3.7, 3.3 and 3 mmHg, respectively. The ocular hypotensive response was significant at all doses and lasted for at least 6 hours at doses of 0.5 and 0.1%. In addition, a significant contralateral effect was also observed at all doses tested.

What is claimed is:

1. A compound of structural formula I:

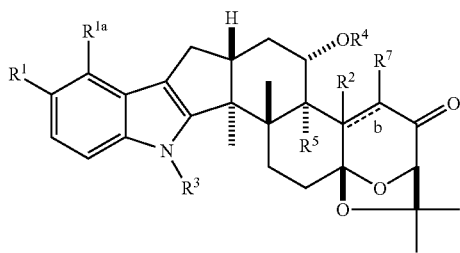

I or a pharmaceutically acceptable salt, enantiomer, diastereomer, tautomer or mixture thereof, wherein, $R^1$ and $R^{1a}$ independently are:

(a) H, (b) $C_{1-6}$ alkyl (c)

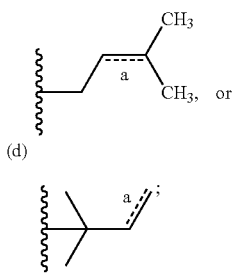

(d)

$R^2$ is:
(a) $CO_2C_{1-6}$alkyl,
(b) H,
(c) OH, or
(d) $C_{1-6}$alkyl,
when a double bond is not present at b;

$R^3$ is:
(a) H,
(b) (C=O)O$C_{1-6}$alkyl or
(c) $C_{1-6}$alkyl optionally substituted with OH, N($R^6$)$_2$, or $CO_2R^6$;

$R^4$ is
(a) H, provided that $R^3$ is not H,
(b) $C_{1-6}$alkyl optionally substituted with OH, N($R^6$)$_2$, or $CO_2R^6$ or (c)

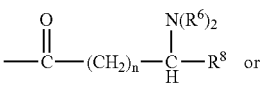

(d)

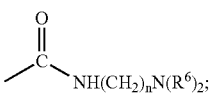

$R^5$ is:
(a) H,
(b) OH, or
(c) $OC_{1-6}$alkyl;

$R^6$ is:
(a) H, or
(b) $C_{1-6}$alkyl;

$R^7$ is H, or $C_{1-6}$alkyl optionally substituted with OH, N($R^6$)$_2$, or $CO_2R^6$;

$R^8$ is H, $C_{1-6}$alkyl, $CH_2$-phenyl, $CH_2$-hydroxyphenyl, $CH_2$-indolyl, $CH_2$-imidazolyl, $CH_2OR^6$, $CH(OR^6)CH_3$, $(CH_2)_nC(O)NR^6$, $(CH_2)_nCO_2R^6$, $(CH_2)_nSR^6$, $(CH_2)_n(N^+R^6)_3$, n is 0-4, and

----- is a double bond optionally and independently present at a or b.

2. A compound according to claim 1 wherein $R^1$, $R^{1a}$ and $R^3$ are hydrogen.

3. A compound according to claim 1 wherein $R^4$ is

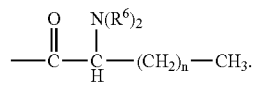

4. A compound according to claim 1 wherein $R^2$ and $R^7$ are hydrogen and $R^4$ is

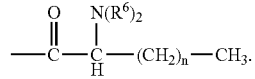

5. A compound which is:

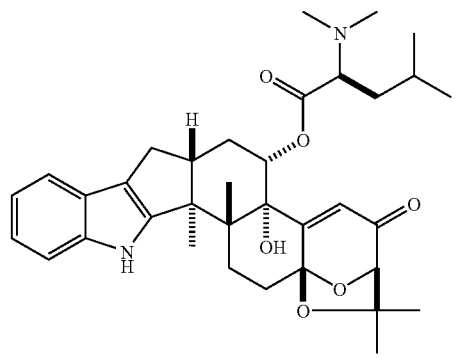

or a pharmaceutically acceptable salt, enantiomer, diastereomer, tautomer or mixture thereof.

6. A composition comprising a compound of formula I as recited in claim 1 and a pharmaceutically acceptable carrier.

* * * * *